(12) United States Patent
Johnson et al.

(10) Patent No.: US 6,689,796 B1
(45) Date of Patent: Feb. 10, 2004

(54) RODENTICIDAL COMPOSITION

(75) Inventors: Roger Johnson, St. Michael's Industrial Estate Widnes (GB); Malcolm Hadler, St. Michael's Industrial Estate Widnes (GB)

(73) Assignee: Sorex Limited, St. Michael's Industrial Estate Widnes (GB)

( * ) Notice: Subject to any disclaimer, the term of this patent is extended or adjusted under 35 U.S.C. 154(b) by 142 days.

(21) Appl. No.: 09/980,497

(22) PCT Filed: Jun. 1, 2000

(86) PCT No.: PCT/GB00/01987

§ 371 (c)(1),
(2), (4) Date: May 10, 2002

(87) PCT Pub. No.: WO00/74486

PCT Pub. Date: Dec. 14, 2000

(30) Foreign Application Priority Data

Jun. 2, 1999 (GB) ............................................. 9912697

(51) Int. Cl.[7] ........................ A61K 31/44; A01N 25/00
(52) U.S. Cl. ....................................... 514/332; 424/405
(58) Field of Search ........................... 424/405; 514/332

(56) References Cited

U.S. PATENT DOCUMENTS 4,140,778 A    2/1979   Dreikorn ................... 424/263

FOREIGN PATENT DOCUMENTS

| EP | 0 109 697 A | | 5/1984 |
| GB | 1 363 415 A | | 8/1974 |
| GB | 1363415 | * | 8/1974 |

* cited by examiner

*Primary Examiner*—Alton N. Pryor
(74) *Attorney, Agent, or Firm*—Lahive & Cockfield, LLP; Anthony A. Laurentano, Esq.; DeAnn F. Smith, Esq.

(57) ABSTRACT

A rodenticidal composition comprises a carrier together with a rodenticidally effective amount of a compound having formula (I) wherein $R^1, R^2, R^3, R^4, R^5, R^6, R^7$ and $R^8$ are the same or different halogen selected from F, Cl and Br atoms. The preferred compound is bis(2,3,5,6-tetrafluoro-4-pyridyl)amine. The compounds of formula (I) are toxic to rodents, particularly rats, and yet have smell and taste acceptable to rodents.

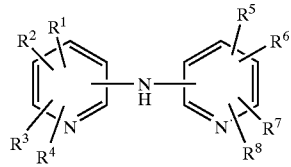

(I)

3 Claims, No Drawings

RODENTICIDAL COMPOSITION

This Application is a 371 of PCT/GB00/01987 filed Jun. 1, 2000.

The present invention relates to new rodenticidal compositions containing certain halogenated bis-pyridyl amine compounds am rodenticidally-active materials. It also relates to new rodent baits containing said halogenated bis-pyridyl amine compounds.

Infestations of rodents, particularly rats, cause serious problems for people close to the locality of there infestations Rats, for instance, cause damage to food crops in store and in the field and represent a health hazard due to the various diseases which they can carry control and elimination of such infestations is, thus, necessary.

Many poisons for rodents are known. However, to be useful in the control and elimination of infestations of rats, a poison has to meet certain criteria in terms of its properties. For instance, it has to be sufficiently toxic such that the consumption of a relatively small amount of bait containing will be fatal for the rat. It also has to have a smell and a taste which is acceptable to the rat or which can be masked by the smell and taste of the bait in which it is employed. It should also be easy and safe for humans.

According to the present invention there is provided a rodenticidal composition comprising a carrier together with an effective amount of rodenticidally-active compound having the formula I

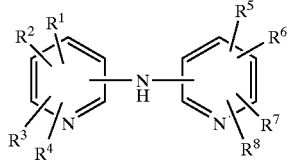

wherein $R^1$, $R^2$, $R^3$, $R^4$, $R^5$, $R^6$, $R^7$ and $R^8$ are the same or different halogen selected from F, Cl and Br atoms. According to a preferred embodiment the amine group in formula I is attached to the two halogenated pyridyl groups at the 4-position. Especially preferred, for use in the present invention, is the compound bis (2,3,5,6-tetrafluoro-4-pyridyl)amine.

Compounds of the formula I above have been discovered by the present inventors to be particularly toxic to rodents, particularly rats, and to have smell and taste that are non-repellent such as to be palatable to rodents.

In the rodenticidal composition the active halogenated bis-pyridyl amine compound is employed in or with a solid carrier which is consumable by the rodents. Such carriers must, like the active compounds, be pallatable to rodents. Typically the carriers will be food items to act as bait for the rodent and these are known generally in the art. Examples of food items that can be used as carriers for the active halogenated bis-pyridyl amine compounds in the present invention include cereal grains, oatmeal, vegetables, biscuits, sugar and molasses.

The compositions of the invention will generally contain up to 200 ppm, and preferably from 20 to 100 ppm of the active halogenated bis-pyridyl amine compound. It is further possible to incorporate into the rodenticidal composition one or more other rodenticidally-active materials, such as anticoagulant-type substances. The incorporation of other active materials into the composition may allow for the use of smaller doses of the halogenated bis-pyridyl amine compounds.

The active halogenated bis-pyridyl amine compounds of Formula I above, especially the compound bis(2,3,5,6-tetrafluoro-4-pyridyl)amine, are particularly useful as the poison component of a rodent bait in particulate form wherein each particle provides a lethal dose of active compound with respect to an adult rodent of the species for which the bait is intended and wherein each particle has a size which allows the rodent species for which the bait is intended to take the particle into its mouth without prior nibbling.

Thus, the present invention further provides a rodent bait comprising food and a poison, said poison being wholly in the form of, or contained in, one or more discrete poison-providing particles of such activity with respect to the rodent species for which the bait is intended that each poison-providing particle provides a lethal dose with respect to an adult rodent of that species, each poison-providing particle being substantially homogeneous and being of a particle size which is such that a rodent of the species for which the bait is intended will take the particle into its mouth without prior nibbling, wherein the poison comprises a compound having the formula I:

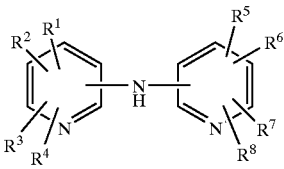

wherein $R^1$, $R^2$, $R^3$, $R^4$, $R^5$, $R^6$, $R^7$ and $R^8$ are the same or different halogen selected from F, Cl and Br atoms. According to an especially preferred embodiment the active compound used in the rodent bait is bis(2,3,5,6-tetrafluoro-4-pyridyl)amine on account of its high toxicity to rodents. Thus, each particle of the bait is ingested orally as an individual particle; the required particle size can be determined by routine experiment. The term "lethal dose" means a dose which normally is capable of killing an adult rodent of the species concerned when taken orally thereby; to those in the art this means a dose which presents an insignificant chance of survival to the largest rodents of the species concerned which is likely to be encountered.

It will be appreciated, therefore, that this aspect of the present invention is predicated on the concept of concentrating the poison component of the bait in particles each of which is lethal per se, and ensuring that the poison particles are taken as a whole into the mouth of the rodent, i.e., without prior nibbling of the poison particles. As a result the rodent feeds on the bait and consumes the food component thereof, which it can nibble or not depending on its particle size, until sooner or later it comes to a poison particle. When it does so, it consumes that particle whole, and once having it into its mouth and swallowed it, death follows inevitably in view of the lethal dose nature of the particle. In short the rodent either consumes innocuous edible material or a lethal dose of poison. This concept was first proposed in EP-A-0109697. In the present invention, however, use is, made of the compounds of the formula I, especially bis(2,3,5,6-tetrafluoro-4-pyridyl)amine, which have the characteristic that a delay occurs between ingestion of the poison particle and death. It has been observed that a rat will be suspicious of a food source if it sees another which is dead or clearly ill close to that food source. Because a rat which has ingested bait containing a lethal dose of bis(2,3,5.6-tetrafluoro-4-pyridyl)amine can take a few hours, typically 4 to 12 hours, before developing visible symptoms of poisoning other rats will not associate the symptoms of a poisoned rat with the bait and will not, therefore, become bait shy. Thus, whereas as the use of poisons which give no significant delay between ingestion and death becomes less successful as time passes since the bait was first put down, and which typically control only 50% of an infestation of rats, the use of the present invention can give at least 97% control of an infestation of rats in 4 nights;

This approach to the formulation of rodent baits has the advantage that the bait as a whole need only comprise relatively few lethal particles in order to be effective against a number of rodents. Also, the inability to detect the presence of lethal particles results in the rodent feeding normally without bait shyness So that even if it does not happen to consume a poison particle at the first feed, it will not be deterred from feeding again on the same kind of bait.

The present invention makes it possible to use, safely, rodent poisons which are lethal in very small quantities. Hitherto, the poison content of acute baits, in which the poison is homogeneously distributed throughout the food component in accordance with conventional practice has normally been in the concentration range 0.2 to 2.0% (2000 to 20,000 ppm). This is a high concentration from the environmental hazard point of view. In contrast, the maximum concentration of poison envisaged in carrying out the present invention is about 200 ppm, typically 20–80 ppm.

Whilst it is possible for the bait to include only one such poison particle, normally it will contain a number of such particles although a lethal particle taken orally by the rodent will kill it, a larger mammal such as a dog (for which the lethal dose would be much larger) happening to feed on the bait would feel sub-lethal symptoms rapidly and stop eating or would not be able to find and eat a significant number of baits and would never reach a lethal level. Baits in accordance with the invention can be formulated so as to be specific to particular rodents. For example, an adult rat weighing 250 grams will eat about 20 grams of food per day. Each bait for rats could comprise say 200 grams and could contain sufficient poison particles to kill say 10 rats. On a one per rat basis that would require 10 such particles because if the particles are distributed as homogeneously as possible in the food component of the bait, on average a rat will come to one and consume it in the course of eating 20 grams. Baits for mice would contain particles of smaller size.

EXAMPLES

Toxic particles were made up according to the following formulation A:

| Formulation A | % by weight |
| --- | --- |
| bis(2,3,5,6-tetrafluoro-4-pyridyl)amine | 80 |
| Gelatine | 15 |
| Sugar | 4.9 |
| *Water Blue 177725 | 0.1 |

*colourant to enable identification of the toxic particles in the final bait mix.

The particles were produced by wetting a mixture having the above formulation with water to form a stiff paste. This paste was extruded through a nozzle and the extrudate was cut into even lengths to produce pellets having average (cylindrical) dimensions 0.85×0.85 mm. The pellets were air dried and sieved to remove fines. After drying, the average weight of the compound in the pellets was 0.4 mg.

The pellets of Formulation A were dispersed into a bait base whose composition was:

| | % by weight |
| --- | --- |
| bis(2,3,5,6-tetrafluoro-4-pyridyl)amine | 0.004 or 0.008 |
| Water Blue 177725 | 0.025 |
| Sugar | 5.0 |
| Commercial Stabilised Oatmeal | balance |

The pellet dispersion rate was one per five grams (80 ppm) to make a bait designated WL/80 and one per ten grams (40 ppm) to make a bait designated WL/40.

Field trials were carried out using the present invention. Four trial sites were chosen as representative of agricultural types with medium infestations of *Rattus norvegicus* (eg. 200–250 rats). The sites were divided into two groups of four (A and B) with two treatments (WL/40 and WL/80) per group.

| Group A: | 2 farms WL/40, 2 farms WL/80 |
| --- | --- |
| Group B: | 2 farms WL/40, 2 farms WL/80. |

The treatment was carried out using a conventional surplus or continuous baiting technique Bait trays were laid in protected situations sited strategically throughout the infested area, the number of trays on each site (eg 30–60) depending on the extent of the infestation.

100 g of bait (WL/40 or WL/80) was placed in each tray. The following day (treatment day 1) the baits were checked visually for takes, weighed to the nearest 2.0 g and replenished to an amount sufficient to avoid a complete take subsequently. Similar checks were made daily for a period of 14 days. At each visit during the treatment tracking tiles were recorded and freshly coated with tracking powder. All dead rodents were collected daily, sexed and weighed.

Results

On all four sites the first four nights were critical in controlling the bulk of the infestations, with a mean of 97.6 control being achieved (this being based on track score). On the first night a large percentage or takes of less than 2 g (PO) were recorded and on two of the sites the percentage of weighable takes to PO takes was less than half.

Subsequent track scores rose on one site but declined on 3 others which was taken as an indication that the infestations at those sites had started to decline. Supplementary tracking patches placed in previously active runs confirmed that activity had reduced markedly. Complete control (100%) was achieved at one site only with high levels of control being obtained on the other three sites (98.6%, 99% and 97.3%). The mean level of control over four sites in the full treatment period was 98.7%. The level of control achieved was, thus, significantly better than could be achieved using conventional (anticoagulant) rodenticide which would not have ben expected to achieve >90% control in less than 10 days on the sites where the treatment was carried out. The speed at which clearance of the rodent infestation was achieved in the example above is a particular advantage of the present invention since the faster clearance can be achieved the less time there tis for rodents to continue damage and disease transmission and for the bait to be exposed hence reducing any environment impact.

What is claimed is:

1. A method of killing rodents comprising administering to a rodent a rodenticidally-effective amount of a compound having the formula I:

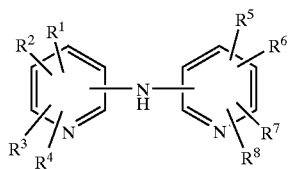

wherein $R^1$, $R^2$, $R^3$, $R^4$, $R^5$, $R^6$, $R^7$ and $R^8$ are the same or different halogens selected from F, Cl and Br atoms.

2. The method according to claim 1, wherein the compound has the formula:

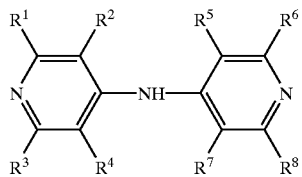

wherein $R^1$, $R^2$, $R^3$, $R^4$, $R^5$, $R^6$, $R^7$ and $R^8$ are as defined in claim 1.

3. The method according to either claim 1 or claim 2, wherein each of $R^1$, $R^2$, $R^3$, $R^4$, $R^5$, $R^6$, $R^7$ and $R^8$ is an F atom.

* * * * *